(12) United States Patent
Hamazaki et al.

(10) Patent No.: US 8,038,604 B2
(45) Date of Patent: Oct. 18, 2011

(54) ENDOSCOPE DISTAL END COVER, ENDOSCOPE INCLUDING THE SAME, AND METHOD FOR REMOVING ENDOSCOPE DISTAL END COVER

(75) Inventors: Masanori Hamazaki, Hachioji (JP); Seiji Kitano, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 722 days.

(21) Appl. No.: 11/789,231

(22) Filed: Apr. 24, 2007

(65) Prior Publication Data

US 2007/0246506 A1    Oct. 25, 2007

(30) Foreign Application Priority Data

Apr. 25, 2006  (JP) .................. 2006-121209

(51) Int. Cl.
  *A61B 1/00*  (2006.01)
  *A61B 1/04*  (2006.01)
(52) U.S. Cl. .................. 600/127; 600/107; 600/129
(58) Field of Classification Search .................. 600/127, 600/107, 121–125, 129, 104, 106, 155–159
  See application file for complete search history.

(56) References Cited

U.S. PATENT DOCUMENTS

| | | | | |
|---|---|---|---|---|
| 4,343,908 A | * | 8/1982 | Faulstich et al. | 501/78 |
| 4,881,810 A | * | 11/1989 | Hasegawa | 356/241.5 |
| 5,104,379 A | * | 4/1992 | Nakamura et al. | 604/111 |
| 5,662,588 A |   | 9/1997 | Iida |   |
| 5,730,701 A | * | 3/1998 | Furukawa et al. | 600/127 |
| 5,860,913 A | * | 1/1999 | Yamaya et al. | 600/127 |
| 5,865,726 A | * | 2/1999 | Katsurada et al. | 600/127 |
| 6,916,284 B2 | * | 7/2005 | Moriyama | 600/127 |
| 2008/0103357 A1 | * | 5/2008 | Zeiner et al. | 600/104 |

FOREIGN PATENT DOCUMENTS

| | | |
|---|---|---|
| JP | 08-140924 | 6/1996 |
| JP | 2003-102668 | 4/2003 |

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscope distal end cover includes a cover portion provided with a coupling port for covering at least a part of an outer circumferential portion of a distal end portion main body configuring an insertion portion of an endoscope; an opening portion for allowing a surface of the distal end portion main body to be in communication with outside when the cover portion is disposed on the distal end portion main body; a finger-hooking portion provided on the cover portion and located away from an edge portion of the coupling port by a predetermined distance; a plastic-deformation portion formed adjacent to the finger-hooking portion and along a predetermined direction of the cover portion; and convex portion engaged with an engaging portion provided to the distal end portion main body, the convex portion being provided on an inner surface of the cover portion adjacent to the plastic-deformation portion.

26 Claims, 11 Drawing Sheets

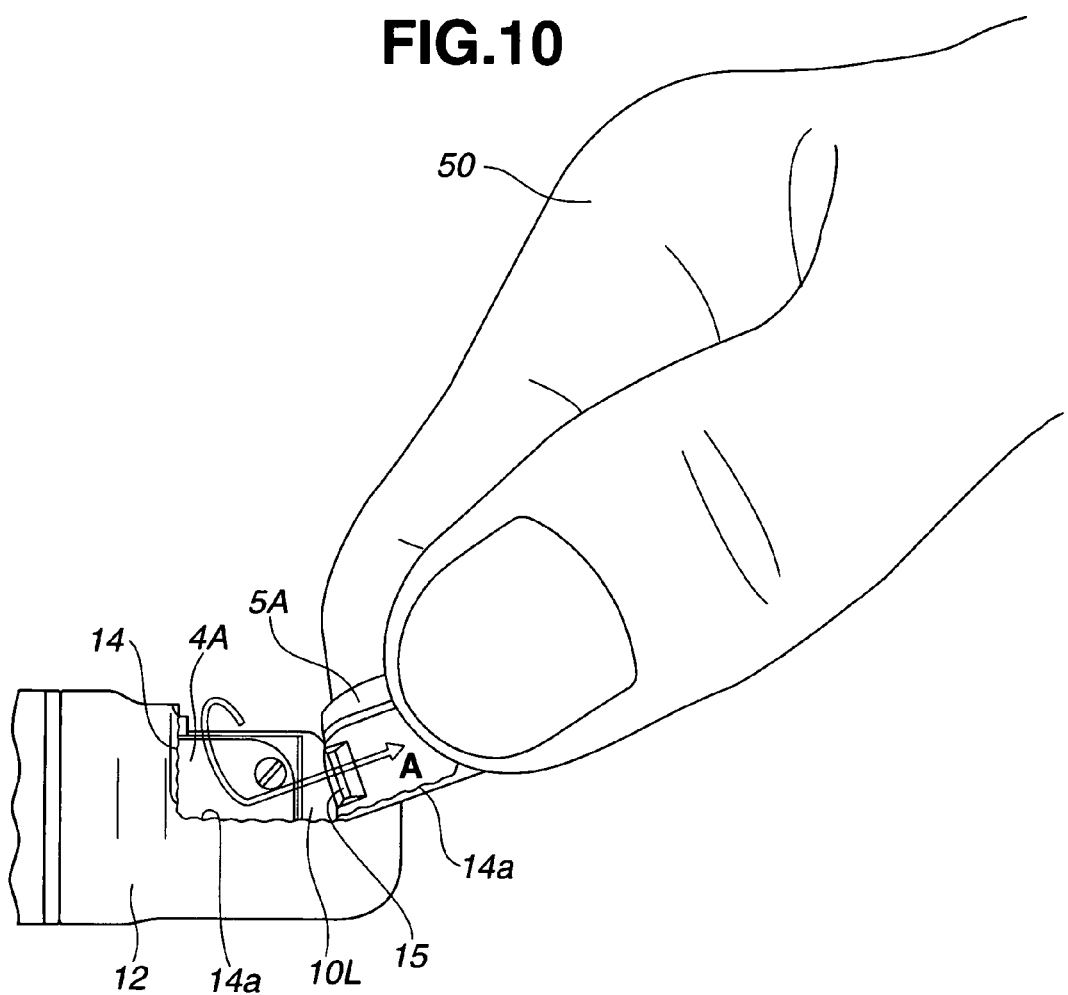
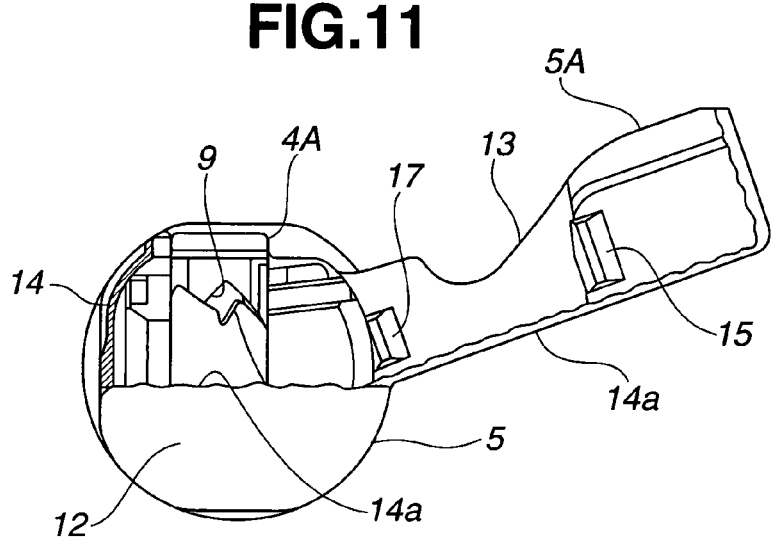

ENDOSCOPE DISTAL END COVER, ENDOSCOPE INCLUDING THE SAME, AND METHOD FOR REMOVING ENDOSCOPE DISTAL END COVER

CROSS REFERENCE TO RELATED APPLICATION

This Application claims benefit of Japanese Application No. 2006-121209 filed in Japan on Apr. 25, 2006, the contents of which are incorporated by this reference.

BACKGROUND OF THE INVENTION

1. Field of the Invention

The present invention relates to an endoscope distal end cover for covering a distal end main body configuring an insertion portion of an endoscope, an endoscope including the endoscope distal end cover, and a method for removing the endoscope distal end cover.

2. Description of Related Art

Generally, an endoscope includes an operation portion grasped by a user for performing various operations, and an insertion portion. The insertion portion includes a flexible tube portion having flexibility which is extended from the operation portion, a bending portion continuously provided at a distal end of the flexible tube portion, and a rigid distal end portion continuously provided at a distal end of the bending portion. The bending portion is bendable, for example, in right/left, up/down directions by an operation of the operation portion.

The distal end portion is provided with an illumination window, an observation window, a nozzle for spouting a fluid to clean the observation window, forceps port which is a lead-out port for various treatment instruments. The distal end portion includes a distal end portion main body and a distal end cover. The distal end cover is mounted for the purpose of insulating the distal end portion main body, or securing airtightness of the distal end main body. The distal end cover is adhered and fixed to the distal end main body so as not to fall off from the distal end main body.

The endoscope is cleaned and disinfected after use from a viewpoint of hygienic control. It is known that, in a case of cleaning the distal end portion of the endoscope, specifically, cleaning a treatment instrument insertion channel of the endoscope for example, a distal end port is exposed by removing the distal end cover and easily cleaned. Furthermore, inside of the distal end portion main body can be also easily cleaned by removing the distal end cover from the distal end portion main body.

Conventionally, many endoscopes including detachable distal end covers have been proposed in consideration of a cleanability of the distal end portion. For example, Japanese Unexamined Patent Application Publication No. 2003-102668 discloses an endoscope provided with a distal end cap which is prevented from falling off when using the endoscope, and can be easily removed and disposed after use.

In the endoscope, the distal end cap is provided with a tearing guide groove as tearing guide means which serves as a guide when tearing the distal end cap from an edge portion thereof. Furthermore, the endoscope includes, at an inner part of the edge portion of the distal end cap, a tool insertion groove which is a start point when tearing the distal end cap using the tearing guide groove. The tool insertion groove is tearing start-point means, and a tool is inserted from the edge portion of the distal end cap via the insertion groove when tearing the distal end cap.

In the endoscope having such a configuration, the distal end cap can be securely mounted to the distal end portion main body by just pressing the distal end cap thereto. On the other hand, in a mounted state, the distal end cap can be easily removed by tearing and breaking the distal end cap itself and releasing an engaged state between the distal end cap and the distal end portion main body. In addition, re-use of the distal end cap is prevented by tearing and breaking the distal end cap itself, so that a new distal end cap is used for each case, thereby securing hygienic state.

Moreover, in the endoscope including the detachable distal end cover, it is easy to facilitate a configuration in which the distal end cap is prevented from falling off during the use of the endoscope, due to the structure in which the distal end cap can be removed only by breaking the distal end cap itself.

SUMMARY OF THE INVENTION

An endoscope distal end cover according to the present invention includes: a cover portion for covering at least a part of an outer circumferential portion of a distal end portion main body configuring an insertion portion of an endoscope; an opening portion for allowing a surface of the distal end portion main body to be in communication with outside when the cover portion is disposed on the distal end portion main body; a finger-hooking portion provided to the cover portion and located away from an edge portion of the opening portion by a predetermined distance; a plastic-deformation portion formed adjacent to the finger-hooking portion along a predetermined direction of the cover portion; and a convex portion engaged with an engaging portion provided to the distal end portion main body, the convex portion being provided on an inner surface of the cover portion adjacent to the plastic-deformation portion.

The above and other objects, features and advantages of the invention will become more clearly understood from the following description referring to the accompanying drawings.

BRIEF DESCRIPTION OF THE DRAWINGS

FIG. 10 is a side view of the distal end portion in a state where a user is tearing the distal end cover while grasping a finger-hooking portion with the fingers;

FIG. 11 is a front view of the distal end portion in a state where the distal end cover is torn further from the state shown in FIG. 10;

DETAILED DESCRIPTION OF PREFERRED EMBODIMENTS

Hereinafter, embodiments of the present invention will be described with reference to the drawings.

Figure 1:
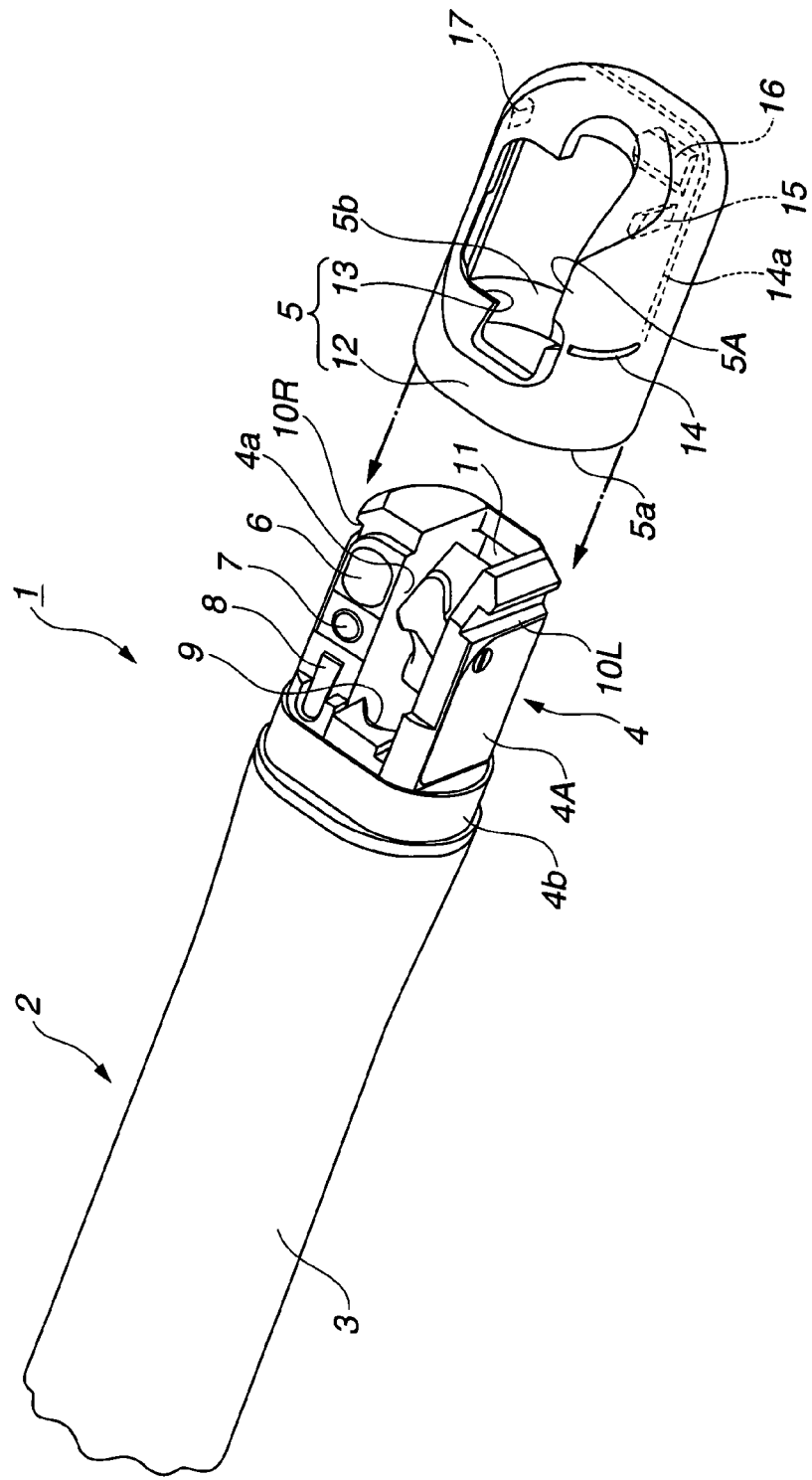
FIG. 1 is a perspective view showing a configuration of a distal end portion of an insertion portion of an endoscope and a distal end cover according to an embodiment of the present invention.
Figure 2:
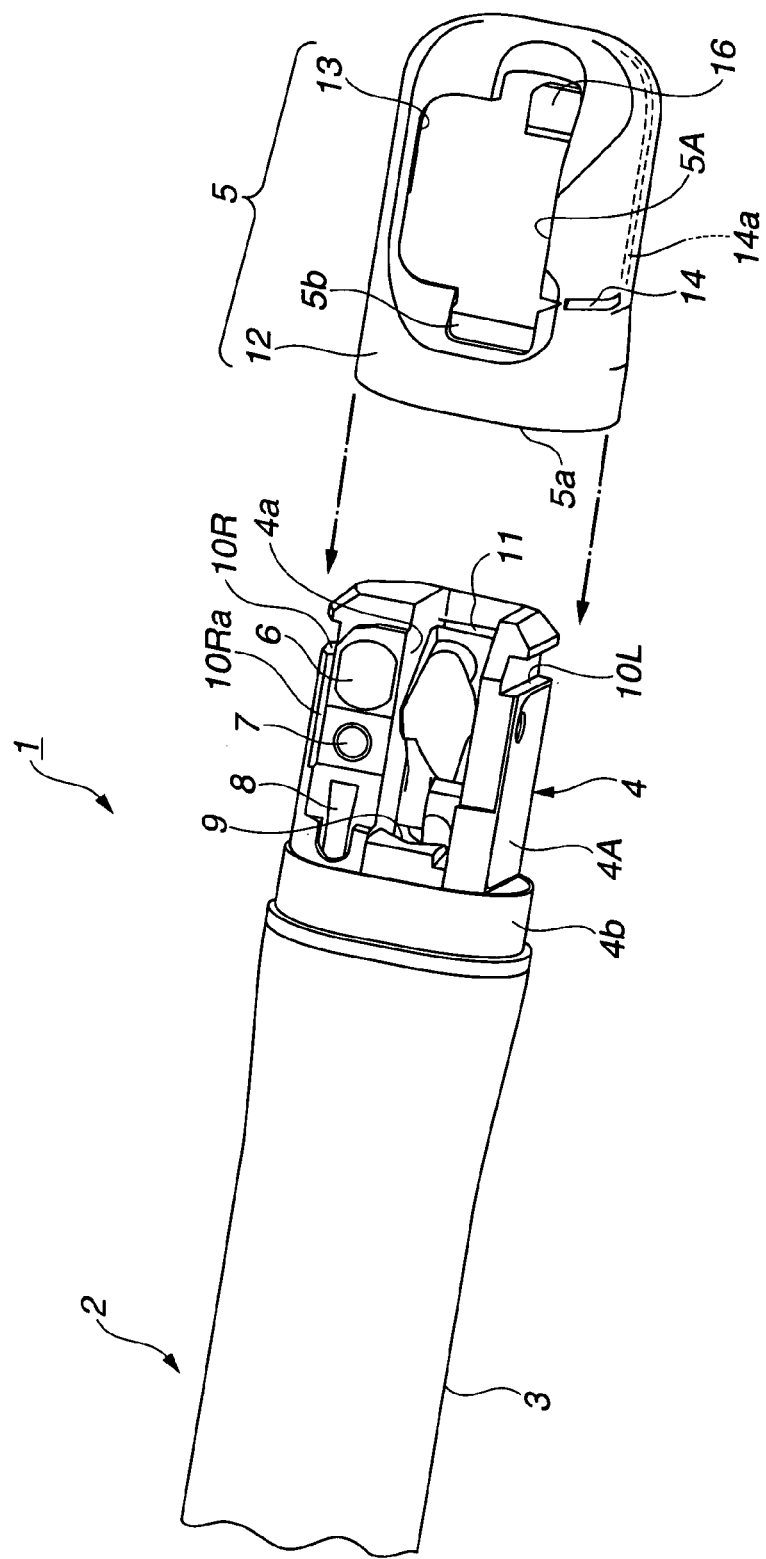
FIG. 2 is a perspective view showing the distal end portion of the insertion portion and the distal end cover of FIG. 1 viewed from an upper direction.
Figure 3:
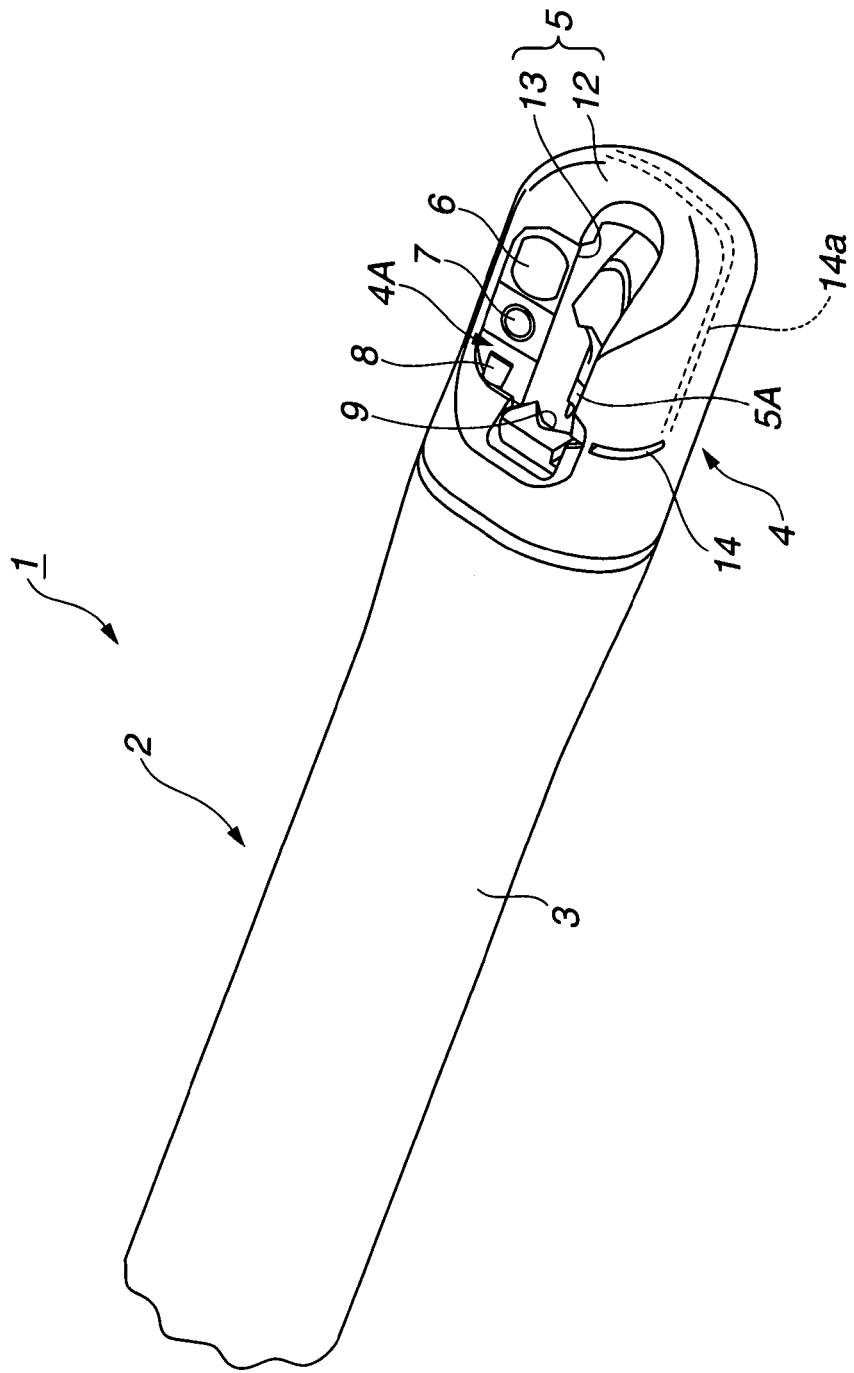
FIG. 3 is a perspective view showing the distal end portion in a case where the distal end cover is mounted to the distal end portion main body, and the insertion portion.

As shown in FIGS. 1 to 3, a side-view endoscope (hereinafter, referred to as an endoscope) 1 of the present embodiment includes an operation portion, not shown, which is grasped by a user for performing various operations, and an insertion portion 2.

The insertion portion 2 includes a flexible tube portion, not shown, having flexibility and extended from the operation portion, a bending portion 3, a distal end portion 4, and an endoscope distal end cover (hereinafter abbreviated as a distal end cover) 5.

The bending portion 3 is continuously provided at the distal end of the flexible tube portion and is bendable in up/down and right/left directions by operating the operation portion. The distal end portion 4 is continuously provided at the distal end of the bending portion 3. The distal end portion 4 includes a rigid distal end portion main body 4A to which a cap-shaped distal end cover 5 is mounted.

The distal end portion 4 configures a distal end of the insertion portion 2 of the endoscope 1, and includes the distal end portion main body 4A, which is made of a metal such as stainless steel for example, to which the distal end cover 5 having an opening portion 13 at a cover portion 12 is mounted.

On one end side of an upper surface which is one of side-surfaces of the distal end portion main body 4A, there are provided the following components in a row, that is, an illumination window 6 from which illumination light for illuminating observation object is irradiated, an observation window 7 into which reflected light from the observation object is introduced, and an air/water feeding nozzle 8 for cleaning the observation window 7 by feeding air, water, or the like.

In addition, in the vicinity of the center of the distal end portion main body 4A, a containing chamber 4a, which is a space for disposing an erecting base or the like, is formed. A forceps port 9 as a lead-out port for various treatment instruments is provided on the side of the bending portion 3 of a concave portion configuring the containing chamber 4a formed in the distal end portion main body 4A.

Note that the illumination window 6 is connected with a light guide as a light transmitting path, not shown, and the observation window 7 is connected with an observation optical system. In addition, the observation optical system includes an objective lens not shown and, for example, a CCD, not shown, as an image-pickup device. The CCD is connected to a circuit substrate, not shown, for extracting image signals. The light guide, the objective lens, the CCD, and the circuit substrate, not shown, are disposed in a storing space, not shown, formed in the distal end portion main body 4A.

At a proximal end portion of the distal end portion main body 4A, which is the side of the bending portion 3, a connecting portion 4b which contacts an inner circumferential surface of a coupling port 5a of the cover portion 12 configuring the distal end cover 5 is provided. The connecting portion 4b is formed in a circular arc shape, for example.

A pair of engaging portions 10L and 10R for engaging with the distal end cover 5 are formed on the left side-surface and the right side-surface which are the side-surfaces of the distal end portion main body 4A, when viewed from the distal end side. The first engaging portion 10L and the third engaging portion 10R are formed on the left side-surface and the right side-surface, respectively. In addition, on the bottom surface of the containing chamber 4a of the distal end portion main body 4A, a second engaging portion 11 for engaging with the distal end cover 5 is formed. Note that the second engaging portion 11 is formed as an opening.

As shown in FIG. 2, a guide groove 10Ra extending in an insertion axis direction of the distal end portion 4 is provided on the right side-surface of the distal end portion main body 4A where the third engaging portion 10R is provided. The guide groove 10Ra guides the distal end cover 5 when mounting the distal end cover 5 to the distal end portion main body 4A, and has a function of preventing the distal end cover 5 from rotating.

To the distal end portion main body 4A configured as described above, the distal end cover 5 is mounted for the purpose of insulating or securing an airtight state. The distal end cover 5 is formed of a resin material such as pliable low-density polyethylene (LDPE) and the like. Note that the material of the distal end cover 5 is not limited to the low-density polyethylene. The distal end cover may be formed of other synthetic resins and elastomer, such as polystyrene resin and the like, or may be formed of rubber material.

The distal end cover 5 has the coupling port 5a which is open at rear end thereof as shown in FIGS. 1 and 2. From the coupling port 5a, the distal end of the distal end portion main body 4A is inserted, and the distal end cover 5 is mounted to the distal end portion main body 4A. A tapered portion 5b is provided, in view of outer diameter of the connecting portion 4b, on the inner circumferential surface in the vicinity of the coupling port 5a. Providing the tapered portion 5b enables the distal end cover 5 to be easily mounted to and securely and firmly attached to the connecting portion 4*b* of the distal end portion main body 4A.

The distal end cover 5 has the illumination window 6, the observation window 7, and the like disposed in the opening portion 13. The illumination window 6 and the observation window 7 are exposed from the opening portion 13, and various treatment instruments are led out via the opening portion 13.

Figure 7:
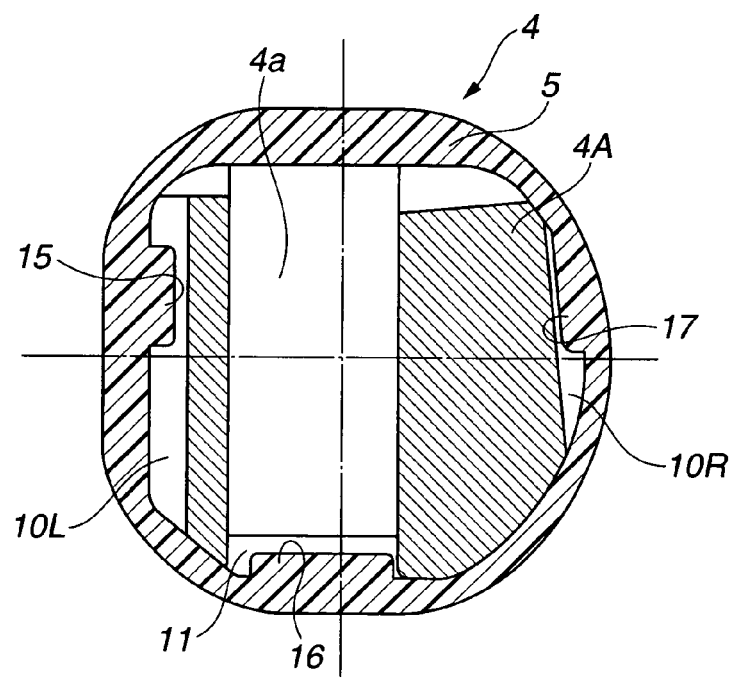
FIG. 7 is a cross-sectional view along VII-VII line of FIG. 4.

In the present embodiment, projection-shaped convex portions 15, 17 are formed as engaging means for integrally fixing the distal end cover 5 and the distal end portion main body 4A. As shown in FIGS. 1 and 7, the first convex portion 15 and the third convex portion 17 are formed on an inner surface of a left side-surface of the distal end cover 5 and on an inner surface of a right side-surface of the distal end cover 5, respectively.

In addition, a projection-shaped second convex portion 16 is formed on a lower inner surface of the distal end surface side of the distal end cover 5.

When the distal end cover 5 is mounted to the distal end portion main body 4A, as shown by the arrows in FIGS. 1 and 2 for example, a user moves the distal end cover 5 toward the distal end portion main body 4A of the endoscope 1 to cover the distal end portion main body 4A with the distal end cover 5. At this time, the distal end cover 5 is mounted, being guided by the guide groove 10Ra of the distal end portion main body 4A.

Figure 5:
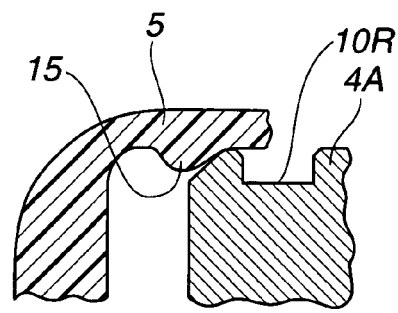
FIG. 5 is a partial cross-sectional view of the distal end portion main body and the distal end cover showing a state before the distal end cover is mounted to the distal end portion main body.
Figure 6:
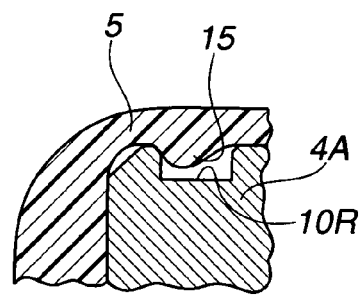
FIG. 6 is a cross-sectional view showing the distal end portion main body and the distal end cover in a state where the distal end cover is mounted to the distal end portion main body and an engaging portion is in an engaged state.

Then, as shown in FIG. 5, when contacting the distal end portion main body 4A, the first convex portion 15 of the distal end cover 5 is deformed by the pressing force generated by the contact. After moving on an outer surface of the distal end portion main body 4A, as shown in FIG. 6, the first convex portion 15 is guided by the first engaging portion 10L of the distal end portion main body 4A to be in an engaged state with the distal end portion main body 4A.

Similarly as the first convex portion 15, when contacting the distal end portion main body 4A, the third convex portion 17 is also deformed by the pressing force generated by the contact. After moving on the outer surface of the distal end portion main body 4A, the third convex portion 17 is guided by the third engaging portion 10R of the distal end portion main body 4A to be in an engaged state with the distal end portion main body 4A.

On the other hand, when the second convex portion 16, which is formed on the bottom surface of the distal end cover 5, contacts the distal end portion main body 4A, the second convex portion 16 is deformed by the pressing force generated by the contact. After moving on the outer surface of the bottom surface side of the distal end portion main body 4A, the second convex portion 16 is guided by the second engaging portion 11 of the distal end portion main body 4A to be in an engaged state with the distal end portion main body 4A.

The first convex portion 15 and the third convex portion 17 are engaged with the first engaging portion 10L and the third engaging portion 10R, respectively, thereby restricting the position of the distal end cover 5 in an insertion axis direction with respect to the distal end portion main body 4A.

Meanwhile, the second convex portion 16 is engaged with the second engaging portion 11, thereby restricting the position of the distal end cover 5 in the insertion axis direction with respect to the distal end portion main body 4A, similarly as mentioned above, and in addition, restricting the position of the distal end cover 5 in a direction perpendicular to the insertion axis direction with respect to the distal end portion main body 4A, in other words, the position of the distal end cover 5 with respect to an outer circumferential direction.

Furthermore, since the tapered portion 5*b* is provided to the distal end cover 5, when mounting is completed as shown in FIGS. 6 and 7, the tapered portion 5*b* of the distal end cover 5 is securely adhered to the connecting portion 4*b* of the distal end portion main body 4A.

Figure 4:
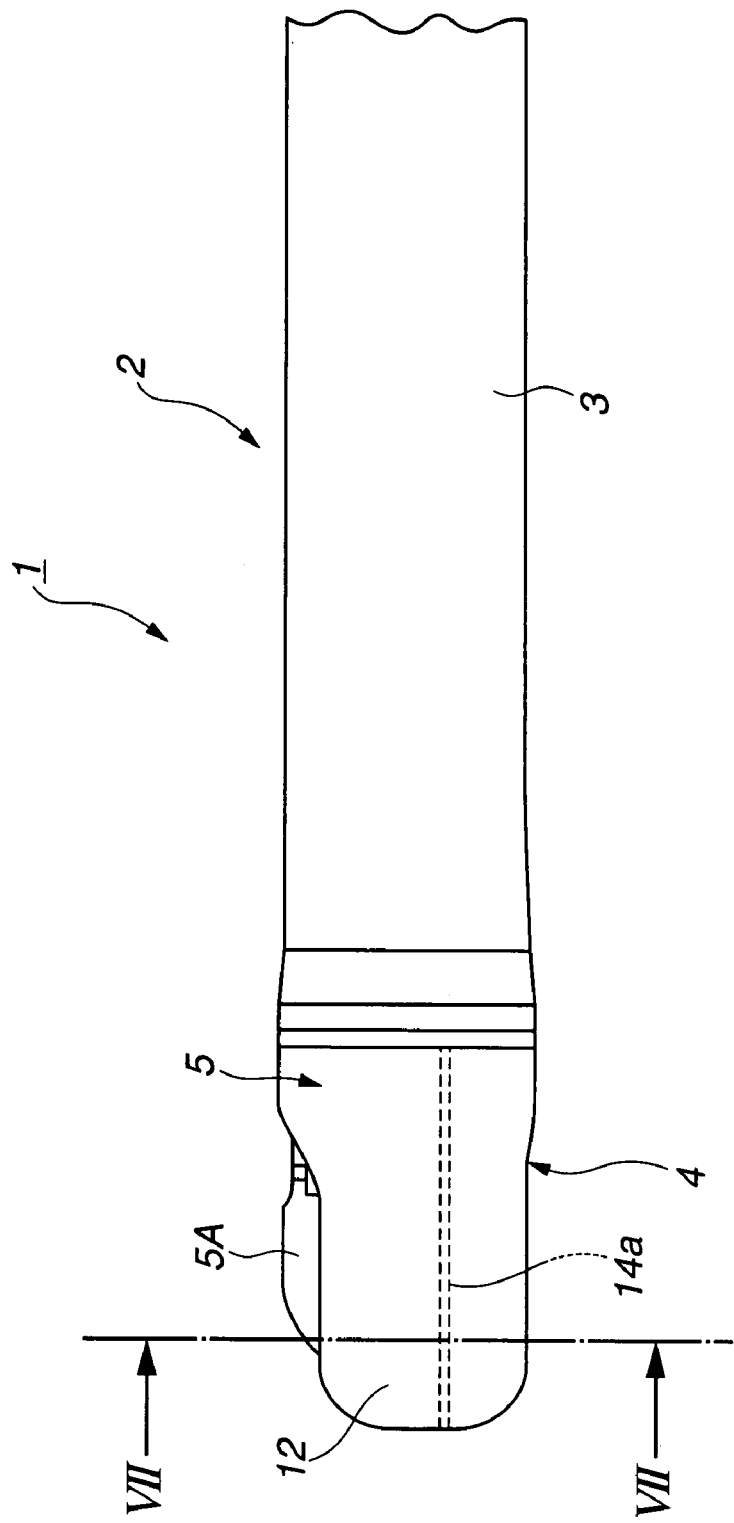
FIG. 4 is a side view of the insertion portion and the distal end portion of FIG. 3.

As a result, the distal end cover 5 is securely engaged with and mounted to the distal end portion main body 4A. Note that the appearances of the insertion portion 2, and the distal end portion 4 in a case where the distal end cover 5 is mounted to the distal end portion main body 4A are shown in FIGS. 3 and 4. In addition, in FIG. 7, stored objects in the distal end portion main body 4A are not shown.

Next, description will be made on a specific configuration for removing the distal end cover 5 from the distal end portion main body 4A, with reference to FIGS. 1 to 4.

As shown in FIGS. 1 to 4, a finger-hooking portion 5A is formed at a predetermined position of the cover portion 12. Specifically, the finger-hooking portion 5A is a part of the vicinity of the opening portion 13 and is formed as at least a part of a stepped portion formed on an outer surface of the cover portion 12. The finger-hooking portion 5A is disposed at a position away from the coupling port 5*a* which is an edge portion of the distal end cover 5, by a predetermined distance.

The finger-hooking portion 5A is a part of an edge portion forming the opening portion 13 of the distal end cover 5. In other words, the finger-hooking portion 5A is formed at the edge portion of the side opposite to the illumination window 6 and the observation window 7 exposed from the opening portion 13. The finger-hooking portion 5A is a part grasped by a user and the like with the fingers, when tearing and removing the distal end cover 5 from the distal end portion main body 4A.

Note that the finger-hooking portion 5A is not necessarily formed as a part of the stepped portion, but only have to be a part of the edge portion of the opening portion 13.

In the distal end cover 5, a thin-walled portion 14, which is a plastic-deformation portion, and a concave groove 14*a* are provided in a predetermined range adjoining the finger-hooking portion 5A. The thin-walled portion 14 and the concave groove 14*a* are plastically deformed at the finger-hooking portion 5A as a starting point, thereby sequentially releasing engaged states by the first convex portion 15, by the second convex portion 16, and by the third convex portion 17.

As shown in FIGS. 1 to 3, or FIG. 4, the thin-walled portion 14 is provided on the side-surface between the finger-hooking portion 5A of the distal end cover 5 and the coupling port 5*a*, and is formed with a predetermined length from the proximal end on the side of the opening portion 13 of the finger-hooking portion 5A toward a lower direction perpendicular to the insertion axis direction of the distal end portion 4.

On the contrary, as shown in FIGS. 1 to 4, the concave groove 14*a* is formed from an inner surface side of one side-surface, via an inner surface side of the distal end surface, to an inner surface side of the other side-surface of the distal end cover 5. One end side of the concave groove 14*a* is positioned at the lower portion side proximal end of the thin-walled portion 14 or in the vicinity thereof. The concave groove 14*a* is formed parallel with the insertion axis direction of the distal end portion 4, in a state where the distal end cover 5 is mounted to the distal end portion main body 4A. In addition, the other end side of the concave groove 14*a* is set at a predetermined position on the other side-surface opposing to the afore-mentioned one end side. That is, the concave groove 14*a* is formed on the inner surface ranging over the whole area from the proximal end or the vicinity of the proximal end of the thin-walled portion 14 to the one side-surface, the distal end surface, and the other side-surface of the distal end cover 5.

Note that, in the present embodiment, the concave groove 14a is provided in the whole area of the one side-surface, the distal end surface, and the other side-surface of the distal end cover 5. However, instead of providing the concave groove 14a in the whole area from the one side-surface, via the distal end surface, to the other side-surface of the distal end cover 5, the concave groove 14a may be provided from the proximal end or in the vicinity of the proximal end of the thin-walled portion 14 to the one side-surface of the distal end cover 5, or may be provided from the proximal end or in the vicinity of the proximal end of the thin-walled portion 14 to a halfway portion of the one side-surface. That is, the concave groove may be provided only to a part of the one side-surface.

In the present embodiment, the thin-walled portion whose thickness is formed smaller than that of the cover portion 12 is provided in the vicinity of the finger-hooking portion 5A of the distal end cover 5, so that a user can easily tear the distal end cover 5 along the thin-walled portion 14 by grasping the finger-hooking portion with the fingers and applying force at hand.

In addition, the concave groove 14a whose thickness is smaller than that of the cover portion 12 is provided such that the one end thereof is located at the proximal end or in the vicinity of the proximal end of the thin-walled portion 14, so that the user can tear the distal end cover 5 along the concave groove 14a in conjunction with the movement of tearing the thin-walled portion 14 by further applying force to the finger-hooking portion 5A.

Then, in the present embodiment, the user first tears the side of the one side-surface of the distal end cover 5 along the concave groove 14a, and thereby the engaged state between the first convex portion 15 and the first engaging portion 10L is released. After that, the user further tears the distal end cover 5, and thereby the engaged state between the second convex portion 16 and the second engaging portion 11 is released. In this state, the restrictions by these two convex portions 15 and 16 are released, so that it is possible to remove the distal end cover 5 from the distal end portion main body 4A in the released state.

After that, the user further tears the side of the distal end surface of the distal end cover 5 along the concave groove 14a, and thereby the engaged state between the second convex portion 16 and the second engaging portion 11 is completely released. After that, the user further tears the side of the other side-surface of the distal end cover 5 along the concave groove 14a, and thereby the engaged state between the third convex portion 17 and the third engaging portion 10R is also released. As a result, the distal end cover 5 is torn and broke, so that the distal end cover 5 can be easily removed from the distal end portion main body 4A.

Note that, it has been described that the plastic-deformation portion has the thin-walled portion 14 and the concave groove 14a provided thereto in the present embodiment. However, the configuration of the plastic-deformation portion is not limited to one in which the thin-walled portion 14 and the concave groove portion 14a are provided. For example, the plastic-deformation portion may have a configuration in which only the thin-walled portion 14 is provided at the same position as that of the distal end cover 5 or a configuration in which only the concave groove 14a is provided. In the configuration, the concave groove 14a may be formed on the inner surface side or on the outer surface side of the distal end cover 5, or on both of the inner surface side and the outer surface side. In any case, it is essential that the thicknesses of the thin-walled portion 14 and the concave groove 14a are formed smaller than that of the cover portion 12.

The position where the thin-walled portion 14 is formed is not limited to the proximal end side of the finger-hooking portion 5A. The thin-walled portion 14 may be provided at any position in the finger-hooking portion 5A, as long as being located in a position where the engaged state between the first convex portion 15 and the first engaging portion 10L is released.

With reference to FIGS. 8 to 11, description will be made on a method for removing the distal end cover 5 of the present invention from the distal end portion main body 4A configuring the insertion portion 2.

Figure 8:
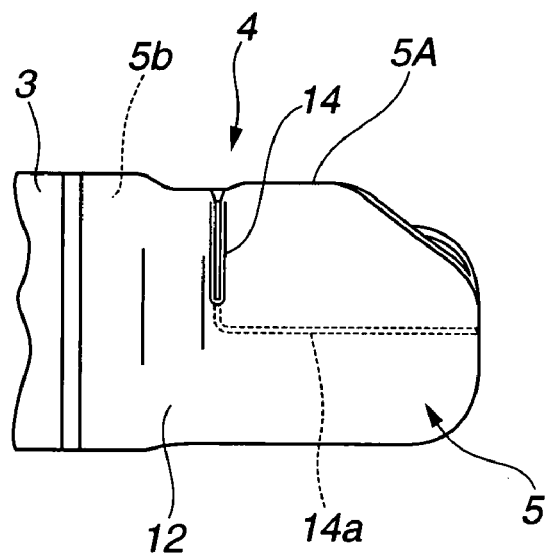
FIG. 8 is a side view showing the distal end portion in a state where the distal end cover is mounted to the distal end portion main body of the insertion portion.
Figure 9:
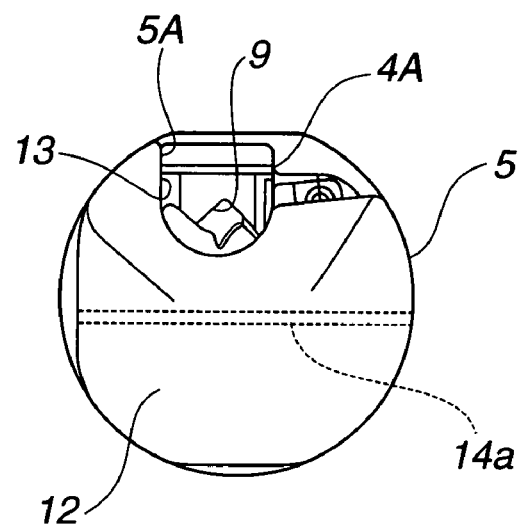
FIG. 9 is a front view showing the distal end portion of FIG. 8 viewed from the forward front.

When the user removes the distal end cover 5 configuring the distal end portion 4 of the endoscope 1 after using the endoscope 1, the distal end cover 5 is mounted to the distal end portion 4 of the insertion portion 2, as shown in FIGS. 8 and 9.

When removing the distal end cover 5, the user grasps the finger-hooking portion 5A provided to the distal end cover 5 with the fingers, and first, the user applies force in the lower direction in the drawing which is perpendicular direction with respect to the insertion axis direction of the distal end portion 4, as shown in FIG. 10. Then, the distal end cover 5 is easily torn along the thin-walled portion 14, since the thin-walled portion 14 whose thickness is smaller than that of the cover portion 12 in the vicinity of the finger-hooking portion 5A of the cover portion 12 configuring the distal end cover 5.

Subsequently, the user applies force for moving the distal end cover 5 in the insertion axis direction which is the direction shown by the arrow A in FIG. 10, grasping the finger-hooking portion 5A. Then, the concave groove 14a provided at the proximal end or in the vicinity of the proximal end of the thin-walled portion 14 is torn in conjunction with the movement of tearing the thin-walled portion 14.

In the present embodiment, the user tears the distal end cover 5 along the concave groove 14a, and as the tearing amount increases, the respective engaged states are released in the following order: the engaged state between the first convex portion 15 and the first engaging portion 10L; the engaged state between the second convex portion 16 and the second engaging portion 11; and the engaged state between the third convex portion 17 and the third engaging portion 10R.

Note that FIG. 10 shows a state where the distal end cover 5 is torn along the concave groove 14a on the one side-surface. In the tearing state, the engaged state between the first convex portion 15 and the first engaging portion 10L is released.

After that, when the user further tears the distal end cover 5 along the concave groove 14a formed on the distal end surface, the distal end cover 5 is torn along the concave groove 14a on the distal end surface as shown in FIG. 11. At this time, in addition, the engaged state between the second convex portion 16 and the second engaging portion 11 is released.

That is, in the state where the engaged state between the first convex portion 15 and the first engaging portion 10L and the engaged state between the second convex portion 16 and the second engaging portion 11 are released, the restrictions of the distal end cover 5 in the insertion axis direction and in the direction perpendicular to the insertion axis direction with respect to the distal end portion main body 4A are released. As a result, it is possible to easily remove the distal end cover 5 from the distal end portion main body 4A.

Then, when the user further tears the distal end cover 5 along the concave groove 14a formed on the other side-surface of the distal end cover 5, the whole of the concave groove 14a formed in the distal end cover 5 is completely torn as shown in FIG. 11, that is, the distal end cover 5 is broken. In the broken state, the engaged state between the third convex portion 17 and the third engaging portion 10R is released.

As a result, the user can easily remove the distal end cover which is broken by tearing the whole concave groove 14a from the distal end portion main body 4A. That is, the distal end cover 5 of the present embodiment is not taken out from the coupling port 5a in the vicinity of the bending portion 3, but removed from the distal end portion main body 4A after tearing and breaking the finger-hooking portion 5A forming a part of the opening portion 13 provided on the upper surface of the distal end cover by grasping the finger hooking portion with the fingers and applying force thereto, without using a tool. Therefore, an outer surface and the like of the bending portion 3 are prevented from being damaged when removing the distal end cover 5.

In addition, the distal end cover 5 is firmly attached to the connecting portion 4b of the distal end portion main body 4A by the tapered portion 5b. Furthermore, the first convex portion 15 is engaged with the first engaging portion 10L, the second convex portion 16 being engaged with the second engaging portion 11, the third convex portion 17 being engaged with the third engaging portion 10R, and thereby the distal end cover is mounted to the distal end portion main body 4A. Therefore, the distal end cover 5 can be surely prevented from falling off from the distal end portion main body 4A during the use of the endoscope.

In addition, because the distal end cover 5 is torn and broken when removed, the user can easily judge that the distal end cover has been used. In other words, the user can easily distinguish the distal end cover after use from the one before use. Consequently, it is possible to resolve the trouble of mistakenly mounting the distal end cover 5 after use to the distal end portion main body 4A.

Furthermore, the distal end cover 5 is disposable and a new distal end cover 5 is always mounted, and thereby the endoscope 1 can be used more hygienically. In addition, it is unnecessary to clean the distal end cover 5 itself, so that cleaning operation of the endoscope is easier.

The distal end cover 5 is mounted along the guide groove 10Ra provided to the distal end portion main body 4A, so that the distal end cover 5 is prevented from unnecessarily rotating with respect to the distal end portion main body 4A. As a result, the distal end cover can be smoothly mounted, thereby greatly improving mountability.

Note that the plastic-deformation portion provided to the distal end cover 5 may be configured as the first modification example or as the second modification example, described later.

Figure 12:
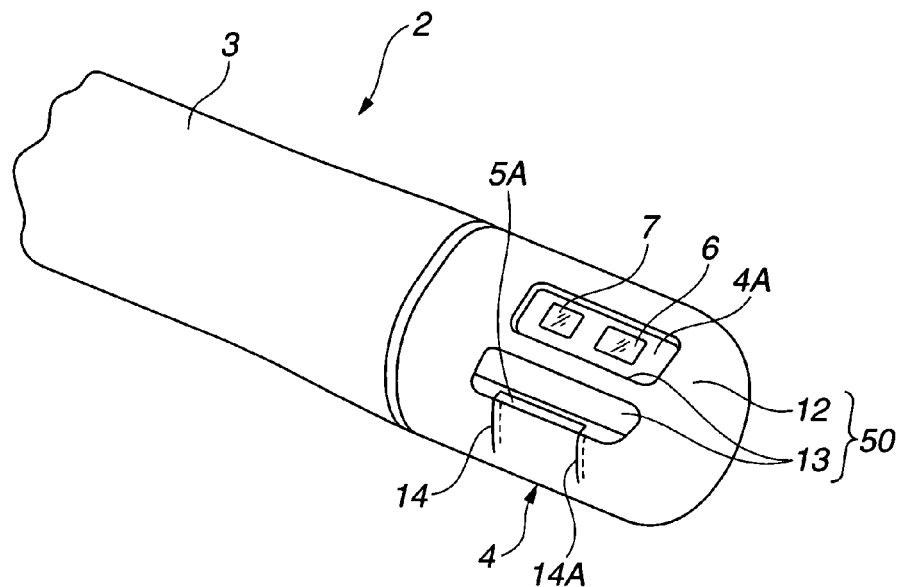
FIG. 12 illustrates a first modification example of a plastic-deformation portion of the distal end cover, and is a perspective view showing the distal end portion of the insertion portion, to which the distal end cover is mounted.
Figure 13:
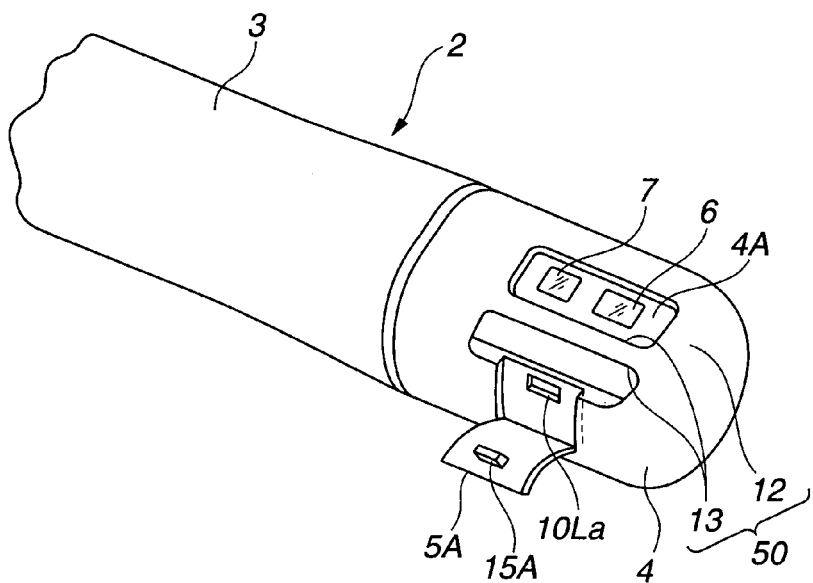
FIG. 13 is a perspective view showing the distal end portion in a state where the distal end cover of the first modification example is torn.

FIGS. 12 and 13 show the first modification example of the plastic-deformation portion provided to the distal end cover.

Note that, in FIGS. 12 and 13, the same reference symbols are assigned to the components that are the same as those of the embodiment described above and a description thereof will be omitted. Only the differences are described.

As shown in FIG. 12, a distal end cover 50 of the present embodiment is provided with a plastic-deformation portion which is the first modification example of the plastic-deformation portion. The plastic-deformation portion of the first modification example is provided with a thin-walled portion 14 and a thin-walled portion 14A. The thin-walled portion 14A is provided on one side-surface of the distal end cover 50 in a positional relation opposing to the thin-walled portion 14. The thin-walled portion 14A is provided parallel with the thin-walled portion 14 from a proximal end side of a finger-hooking portion 5A so as to have the same length with that of the thin-walled portion 14.

Note that, the two thin-walled portions 14 and 14A may be concave grooves provided on an inner surface similarly as the concave groove 14a in the embodiment described above, concave grooves provided on the outer surface, or concave grooves provided on the inner and outer surfaces.

On the inner surface between the thin-walled portion 14 and the thin-walled portion 14A of the distal end cover 50, provided is a convex portion 15A to be engaged with an engaging portion 10La configured by a recession provided in the distal end portion main body 4A. The distal end cover 50 is mounted to the distal end portion main body 4A, and thereby the convex portion 15A is engaged with the engaging portion 10La provided to the distal end portion main body 4A. In a state where the convex portion 15A and the engaging portion 10La are engaged with each other, the movement of the distal end cover 50 in an insertion axis direction and the movement thereof in a direction perpendicular to the insertion axis direction with respect to the distal end portion main body 4A can be restricted.

The distal end cover 50 configured as described above can be broken as a result that a user applies force toward a lower direction perpendicular to the insertion axis direction of the distal end portion 4, grasping the finger-hooking portion 5A of the distal end cover 50 with the fingers, and tears the two thin-walled portions 14, 14A. Consequently, the engaged state between the convex portion 15A and the engaging portion 10La is released, so that the distal end cover 50 can be easily removed from the distal end portion main body 4A.

Figure 14:
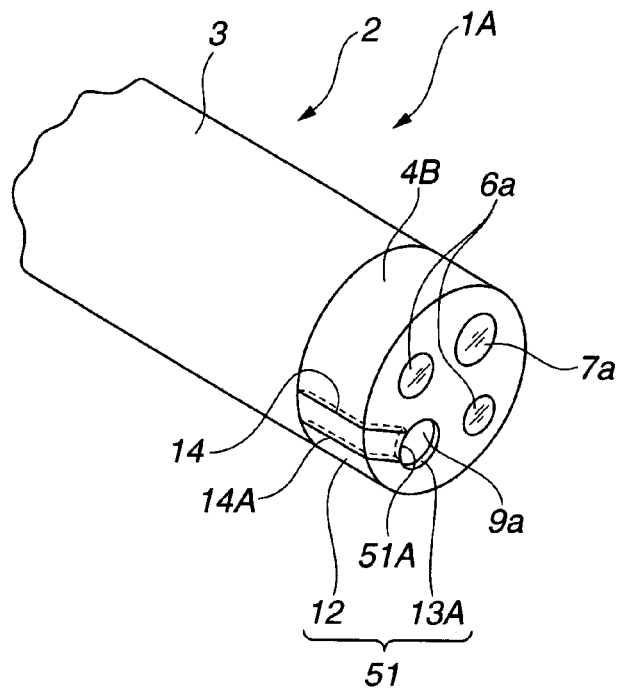
FIG. 14 illustrates a second modification example of the plastic-deformation portion of the distal end cover, and is a perspective view showing the distal end portion in a case where the distal end cover is mounted to the distal end portion of a normal endoscope.
Figure 15:
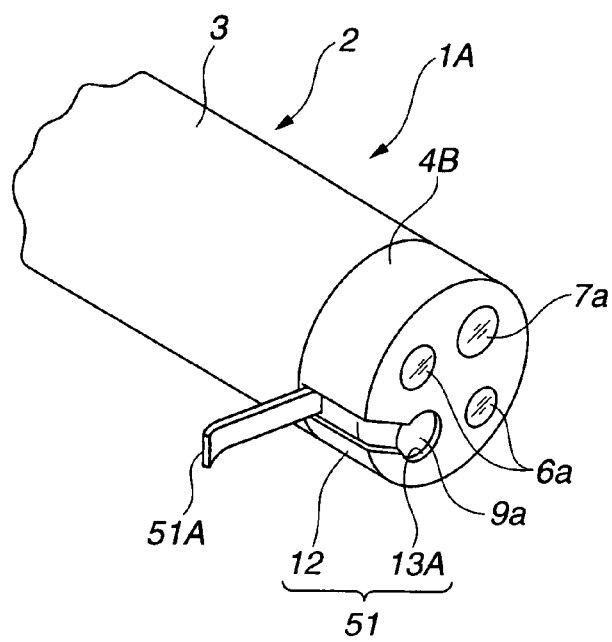
FIG. 15 is a perspective view showing the distal end portion in a state where the distal end cover of the second modification example is torn.

FIGS. 14 and 15 show the second modification example of the plastic-deformation portion provided to the distal end cover. Note that, the same reference symbols are assigned to the components that are the same as those of the embodiment described above and a description thereof will be omitted. Only the differences are described.

As shown in FIG. 14, a distal end cover 51 of the present embodiment is mounted to a direct-view endoscope 1A instead of the side-view endoscope. As is well known, on a distal end surface of a distal end portion 4B of the direct-view endoscope 1A, provided are two illumination windows 6a, an observation window 7a configuring an objective optical system and disposed in the vicinity of the two illumination windows 6a, and a forceps port 9a which is a lead-out port for various treatment instruments.

The distal end cover 51 is mounted to the distal end portion 4B of the endoscope 1A. The distal end cover 51 includes two thin-walled portions 14, 14A configuring the plastic-deformation portion approximately the same as that of the first modification example, and the finger-hooking portion 51A.

In the present embodiment, the finger-hooking portion 51A is configured as a part of an opening portion 13A corresponding to the forceps port 9a provided on the distal end surface. The two thin-walled portions 14, 14A are provided from an edge portion of the opening portion 13A to a rear end side of the one side-surface of the distal end cover 51. The interval between the two thin-walled portions 14, 14A is the width dimension of the finger-hooking portion 51.

Note that, although the two thin-walled portions 14, 14A are provided parallel with each other, it may be configured that the widths of the two thin-walled portions 14, 14A are appropriately changed. In addition, the two thin-walled portions 14, 14A may be concave grooves provided on the inner surface similarly as the concave groove 14a.

Furthermore, though the illustration is omitted, it may be configured that a convex portion to be engaged with an engaging portion, not shown, provided to the distal end portion main body 4B is provided on an inner circumferential surface between the two thin-walled portions 14, 14A of the distal end cover 51. According to the configuration, the distal end cover 51 is mounted to the distal end portion main body 4B, and the convex portion is engaged with the engaging portion, thereby restricting the movement of distal end cover 51 in an insertion axis direction and the movement thereof in a direction perpendicular to the insertion axis direction with respect to the distal end portion main body 4B.

The distal end cover 51 configured as described above can be broken as a result that a user applies force toward a horizontal direction parallel with the insertion axis direction of the distal end portion 4, grasping the finger-hooking portion 51A of the distal end cover 51 with the fingers, and tears the two thin-walled portions 14, 14A. As a result, the distal end cover 51 can be easily removed from the distal end portion main body 4B.

Figure 16:
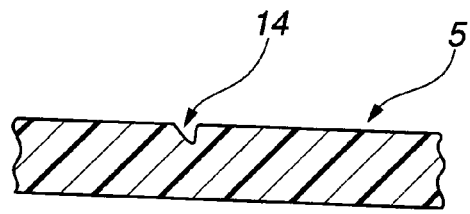
FIG. 16 is a cross-sectional view of the distal end cover in a case where the plastic-deformation portion is formed in a V-groove shape.

Note that, in the above-described embodiment, the first modification example, and the second modification example, the plastic-deformation portion provided to each of the distal end covers 5, 50, and 51 are described as the thin-walled portion 14 or the concave groove 14a. However, the plastic-deformation portion is not limited to the thin-walled portion 14 or the concave groove 14a. For example, as shown in FIG. 16, it may be configured that a thin-walled portion 14 configured in a V-groove shape is provided to the distal end cover 5.

Figure 17:
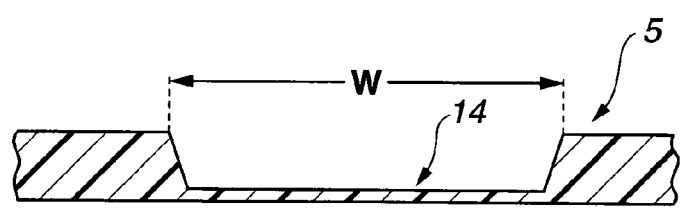
FIG. 17 is a cross-sectional view of the distal end cover showing another configuration example of the plastic-deformation portion.
Figure 18:
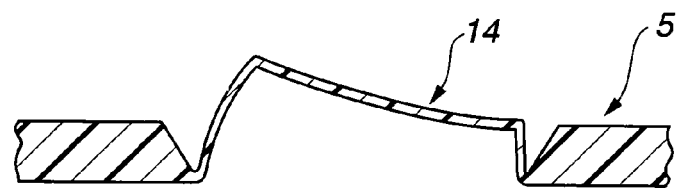
FIG. 18 is a descriptive view describing a plastic-deformation operation of the plastic-deformation portion shown in FIG. 17.

Furthermore, as shown in FIG. 17, the plastic-deformation portion may be configured, provided with a concave portion of a predetermined width W, as a concave groove 14a or as a thin-walled portion 14 having a thin flat bottom portion. The thin-walled portion 14 and the concave groove 14a, which are provided with the concave portion of the width W, are not torn when the distal end cover 5 is removed as described above, but the thin part is stretched as shown in FIG. 18.

That is, when removing the distal end cover 5 from the distal end portion main body 4A, a clearance is formed between the distal end cover and the distal end portion main body 4A as a result that the thin part of the thin-walled portion 14 is stretched. Therefore, the distal end cover 5 can be removed from the distal end portion main body 4A.

Figure 19:
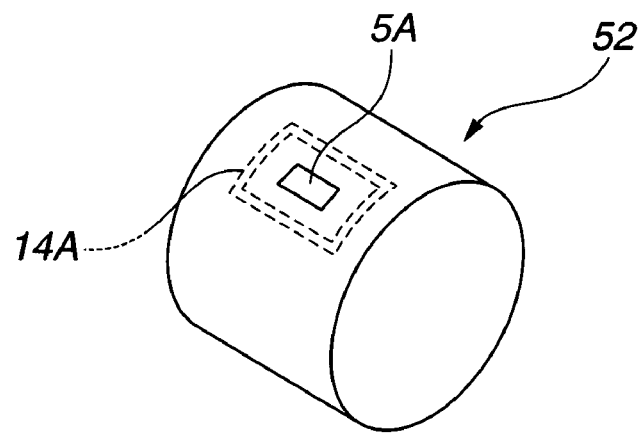
FIG. 19 is a perspective view of the distal end cover including the plastic-deformation portion provided so as to surround the finger-hooking portion.

That is, as described above, the thin-walled portion 14 or the concave groove 14a configuring the plastic-deformation portion is not limited to one that is torn when removing the distal end cover 5. Therefore, as shown in FIG. 19 for example, it may be configured that a finger-hooking portion 5A is provided on a side surface of the distal end cover 52, and a thin-walled portion 14A formed of a member having a plastic-deformation characteristic is so provided as to surround the finger-hooking portion 5A. The thin-walled portion 14A may be a concave groove formed on the inner surface.

Figure 20:
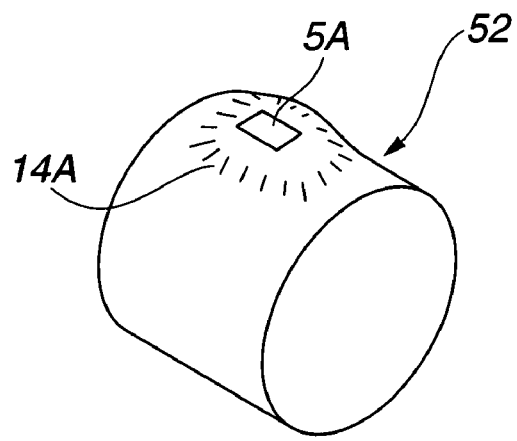
FIG. 20 is a descriptive view describing a plastic-deformation operation of the plastic-deformation portion shown in FIG. 19.

With the distal end cover 52 configured as described above, the thin-walled portion 14A having the plastic-deformation characteristic plastically deforms so as to be picked up as shown in FIG. 20 as a result that the user applies force in a direction away from the circumferential surface of the distal end portion 4 while pinching the finger-hooking portion 5A of the distal end cover 52 with the fingers. As a result, a clearance is formed between the distal end cover and the distal end portion main body, so that the distal end cover 52 can be easily removed from the distal end portion main body.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope distal end cover, comprising:
   a cover portion provided with a coupling port, for covering at least a part of an outer circumferential portion of a distal end portion main body configuring an insertion portion of an endoscope;
   an opening portion for allowing a surface of the distal end portion main body to be in communication with an environment outside of the distal end portion when the cover portion is disposed on the distal end portion main body, the opening portion being formed on the cover portion, the opening portion located away from an edge portion of the coupling port by a predetermined distance;
   a finger-hooking portion which is a part of the opening portion formed on the cover portion and which is a grasping portion located away from the edge portion of the coupling port by a predetermined distance;
   a plastic-deformation portion formed adjacent to the finger-hooking portion including a thin-walled portion having a smaller thickness than the thickness of the cover portion on a side surface between the finger-hooking portion and the coupling port in a direction perpendicular to an insertion axis direction of the cover portion, and a concave groove that extends from adjacent the finger-hooking portion, to an opposite side of the cover portion around the periphery of the cover portion, and having first sections along the insertion axis direction and a second section continuous with the first sections in the direction perpendicular to the insertion axis direction, the plastic deformation portion being torn from a position that is away from the edge portion of the coupling port by a predetermined distance by applying force to the finger-hooking portion; and
   a convex portion engaged with an engaging portion provided to the distal end portion main body, the convex portion being provided on an inner surface of the cover portion adjacent to the plastic-deformation portion.

2. The endoscope distal end cover according to claim 1, wherein the plastic-deformation portion is torn with the finger-hooking portion as a starting point and forms, between the cover portion and the distal end portion main body, a clearance for releasing an engaged state by the convex portion with respect to the engaging portion of the distal end portion main body.

3. The endoscope distal end cover according to claim 1, wherein the finger-hooking portion is at least a part of a stepped portion formed on an outer surface of the cover portion.

4. The endoscope distal end cover according to claim 2, wherein
   the convex portion includes a first convex portion, a second convex portion, and third convex portion which are engaged with the engaging portions of the distal end portion main body, and
   the first convex portion, the second convex portion, and the third convex portion, in a state of being engaged with the engaging portions of the distal end portion main body, restrict at least one of a movement of the endoscope distal end cover in an insertion axis direction and a movement of the endoscope distal end cover in a circumferential direction of the distal end portion main body, the circumferential direction being perpendicular to the insertion axis direction.

5. The endoscope distal end cover according to claim 4, wherein the plastic-deformation portion is torn with the finger-hooking portion as the starting point, and as tearing amount of the plastic-deformation portion increases, engaged states of the convex portions engaged with the engaging portions of the distal end portion main body are released in an order of the first convex portion, the second convex portion, and the third convex portion.

6. The endoscope distal end cover according to claim 2, wherein the plastic-deformation portion is a thin-walled portion formed to have a thickness smaller than a thickness of the cover portion.

7. The endoscope distal end cover according to claim 5, wherein the plastic-deformation portion is a thin-walled portion formed to have a thickness smaller than a thickness of the cover portion.

8. The endoscope distal end cover according to claim 6, wherein the thin-walled portion is a concave groove formed in a groove shape on an inner surface or an outer surface of the cover portion, or on the inner surface and on the outer surface of the cover portion.

9. The endoscope distal end cover according to claim 8, wherein the concave groove is formed on a whole or a part of an inner circumferential surface of the cover portion, along the insertion axis direction of the distal end portion main body and the direction perpendicular to the insertion axis direction.

10. The endoscope distal end cover according to claim 7, wherein the thin-walled portion is a concave groove formed in a groove shape on an inner surface or an outer surface of the cover portion, or on the inner surface and on the outer surface of the cover portion.

11. The endoscope distal end cover according to claim 10, wherein the concave groove is formed on a whole or a part of an inner circumferential surface of the cover portion, along the insertion axis direction of the distal end portion main body and the direction perpendicular to the insertion axis direction.

12. The endoscope distal end cover according to claim 1, wherein
the insertion portion includes a duct through which a treatment instrument is insertable, and the finger-hooking portion configures a part of a circumferential portion of a communication path formed for allowing the duct to be in communication with outside, the communication path being formed on the cover portion.

13. The endoscope distal end cover according to claim 1, wherein the thin-walled portion on the side surface of the plastic-deformation portion is configured to be torn with the finger-hooking portion as the starting point in a direction perpendicular to the insertion axis direction, and wherein the concave groove on the side surface of the plastic-deformation portion is configured to be torn along the insertion axis direction.

14. An endoscope comprising:
a rigid distal end portion main body provided on a distal end side of an insertion portion; and
an endoscope distal end cover, including:
a cover portion provided with a coupling port for covering at least a part of an outer circumferential portion of a distal end portion main body;
an opening portion for allowing a surface of the distal end portion main body to be in communication with an environment outside of the distal end portion when the cover portion is disposed on the distal end portion main body, the opening portion being formed on the cover portion, the opening portion located away from an edge portion of the coupling port by a predetermined distance;
a finger-hooking portion which is a part of the opening portion formed on the cover portion and which is a grasping portion located away from the edge portion of the coupling port by a predetermined distance;
a plastic-deformation portion formed adjacent to the finger-hooking portion including a thin-walled portion having a smaller thickness than the thickness of the cover portion on a side surface between the finger-hooking portion and the coupling port in a direction perpendicular to an insertion axis direction of the cover portion, and a concave groove that extends from adjacent the finger-hooking portion, to an opposite side of the cover portion around the periphery of the cover portion, and having first sections along the insertion axis direction and a second section continuous with the first sections in the direction perpendicular to the insertion axis direction, the plastic deformation portion being torn from a position that is away from the edge portion of the coupling port by a predetermined distance by applying force to the finger-hooking portion; and
a convex portion engaged with an engaging portion provided to the distal end portion main body, the convex portion being provided on an inner surface of the cover portion adjacent to the plastic-deformation portion.

15. The endoscope according to claim 14, wherein the plastic-deformation portion is torn with the finger-hooking portion as a starting point, and forms, between the cover portion and the distal end portion main body, a clearance for releasing an engaged state by the convex portion with respect to the engaging portion of the distal end portion main body.

16. The endoscope according to claim 15, wherein the convex portion includes a first convex portion, a second convex portion, and a third convex portion which are engaged with the engaging portions of the distal end portion main body, and
the first convex portion, the second convex portion, and the third convex portion, in a state of being engaged with the engaging portions of the distal end portion main body, restrict at least one of a movement of the endoscope distal end cover in an insertion axis direction and a movement of the endoscope distal end cover in a circumferential direction of the distal end portion main body, the circumferential direction being perpendicular to the insertion axis direction.

17. The endoscope according to claim 16, wherein the plastic-deformation portion is town with the finger-hooking portion as the starting point, and as tearing amount of the plastic-deformation portion increases, engaged states of the convex portions engaged with the engaging portions of the distal end portion main body are released in an order of the first convex portion, the second convex portion, and the third convex portion.

18. The endoscope according to claim 17, wherein the plastic-deformation portion is a thin-walled portion formed to have a thickness smaller than a thickness of the cover portion.

19. The endoscope according to claim 18, wherein the thin-walled portion is a concave groove formed in a groove shape on an inner surface or an outer surface of the cover portion, or on the inner surface and on the outer surface of the cover portion.

20. The endoscope according to claim 19, wherein the concave groove is formed on a whole or a part of an inner circumferential surface of the cover portion along the insertion axis direction of the distal end portion main body and the direction perpendicular to the insertion axis direction.

21. The endoscope according to claim 15, wherein the plastic-deformation portion is a thin-walled portion formed to have a thickness smaller than a thickness of the cover portion.

22. The endoscope according to claim 21, wherein the thin-walled portion is a concave groove formed in a groove shape on an inner surface or an outer surface of the cover portion, or on the inner surface and on the outer surface of the cover portion.

23. The endoscope according to claim 22, wherein the concave groove is formed on a whole or a part of an inner circumferential surface of the cover portion along the insertion axis direction of the distal end portion main body and the direction perpendicular to the insertion axis direction.

24. The endoscope according to claim 14, wherein the finger-hooking portion is at least a part of a stepped portion formed on an outer surface of the cover potion.

25. The endoscope according to claim 14, wherein
the insertion portion includes a duct through which a treatment instrument is insertable,
and the finger-hooking portion configures a part of a circumferential portion of a communication path formed for allowing the duct to be in communication with outside, the communication path being formed on the cover portion.

26. The endoscope according to claim 14, wherein a direction in which the plastic-deformation portion is torn with the finger-hooking portion as the starting point is a circumferential direction of the cover portion, the circumferential direction being perpendicular to an insertion axis direction of the distal end portion main body.

* * * * *